(12) United States Patent
Lee

(10) Patent No.: US 10,799,133 B2
(45) Date of Patent: Oct. 13, 2020

(54) WEARABLE DEVICE AND CONTROL METHOD THEREFOR

(71) Applicant: Y-BRAIN INC., Daejeon (KR)

(72) Inventor: Kiwon Lee, Seongnam-si (KR)

(73) Assignee: Y-BRAIN INC., Daejeon (KR)

( * ) Notice: Subject to any disclaimer, the term of this patent is extended or adjusted under 35 U.S.C. 154(b) by 313 days.

(21) Appl. No.: 15/500,262

(22) PCT Filed: Jul. 6, 2015

(86) PCT No.: PCT/KR2015/006971
§ 371 (c)(1),
(2) Date: Jan. 30, 2017

(87) PCT Pub. No.: WO2016/021839
PCT Pub. Date: Feb. 11, 2016

(65) Prior Publication Data
US 2017/0215753 A1 Aug. 3, 2017

(30) Foreign Application Priority Data
Aug. 7, 2014 (KR) .................. 10-2014-0101639

(51) Int. Cl.
*A61B 5/04* (2006.01)
*A61N 1/20* (2006.01)
(Continued)

(52) U.S. Cl.
CPC ........ *A61B 5/04001* (2013.01); *A61B 5/0476* (2013.01); *A61B 5/6803* (2013.01);
(Continued)

(58) Field of Classification Search
CPC . A61B 5/04001; A61B 5/0476; A61B 5/6803; A61B 5/0531; A61B 5/117;
(Continued)

(56) References Cited

U.S. PATENT DOCUMENTS

| 2014/0159862 A1* | 6/2014 | Yang ................ A61B 5/1171 340/5.52 |
| 2015/0112153 A1* | 4/2015 | Nahum ............. A61B 5/6803 600/301 |
| 2016/0008632 A1* | 1/2016 | Wetmore ............ A61N 7/00 601/2 |

FOREIGN PATENT DOCUMENTS

| CN | 102016757 A | 4/2011 |
| CN | 102711601 A | 10/2012 |

(Continued)

OTHER PUBLICATIONS

Japanese Office Action dated Nov. 14, 2017, in connection with the counterpart Chinese Patent Application No. 2017-526469.

(Continued)

*Primary Examiner* — Devin B Henson
(74) *Attorney, Agent, or Firm* — Hauptman Ham, LLP

(57) ABSTRACT

A wearable device according to an embodiment of the present disclosure of the present inventive concept, which is worn on a user's head to apply an electrical stimulation to a brain or measure brain waves from the brain, comprises: a wearing identification unit for identifying a worn state of the wearable device using a first sensor module detecting the worn state of the wearable device of a user; an electrode unit for applying an electrical stimulation to a user's brain or measuring brain waves from the user's brain; and a control unit for controlling the electrode unit to start the electrical stimulation or a brain wave measurement on the basis of the identification result by the wearing identification unit.

8 Claims, 11 Drawing Sheets

(51) Int. Cl.
*A61N 1/04* (2006.01)
*A61B 5/0476* (2006.01)
*A61B 5/00* (2006.01)
*A61N 1/36* (2006.01)
*A61B 5/117* (2016.01)
*A61B 5/053* (2006.01)
*A61B 5/1172* (2016.01)
*A61B 5/1171* (2016.01)
*G06F 3/01* (2006.01)

(52) U.S. Cl.
CPC ............ *A61N 1/0456* (2013.01); *A61N 1/20* (2013.01); *A61N 1/36025* (2013.01); *G06F 3/015* (2013.01); *A61B 5/0531* (2013.01); *A61B 5/117* (2013.01); *A61B 5/1172* (2013.01); *A61B 5/1176* (2013.01); *A61B 5/6814* (2013.01); *A61B 5/6843* (2013.01); *A61B 5/6844* (2013.01); *A61B 5/7405* (2013.01); *A61N 1/04* (2013.01); *A61N 1/0484* (2013.01)

(58) Field of Classification Search
CPC ... A61B 5/1172; A61B 5/1176; A61B 5/6814; A61B 5/6843; A61B 5/6844; A61N 1/0456; A61N 1/20; A61N 1/36025; A61N 1/0484; G06F 3/015
See application file for complete search history.

(56) References Cited

FOREIGN PATENT DOCUMENTS

| | | |
|---|---|---|
| CN | 103455746 A | 12/2013 |
| JP | 2007-067782 A | 3/2007 |
| JP | 4465414 B2 | 5/2010 |
| JP | WO2011158481 A1 | 12/2011 |
| KR | 10-1031507 B1 | 4/2011 |
| KR | 10-2013-0125122 A | 11/2013 |
| KR | 10-2014-0080053 A | 6/2014 |

OTHER PUBLICATIONS

International Search Report dated Oct. 7, 2015 corresponding to International Application PCT/KR2015/006971.
Chinese Office Action dated Oct. 19, 2018, in connection with the Chinese Patent Application No. 201580041993.X.

* cited by examiner

WEARABLE DEVICE AND CONTROL METHOD THEREFOR

CROSS REFERENCE TO RELATED APPLICATION

This application claims the priority of Korean Patent Application No. 10-2014-0101639, filed on Aug. 7, 2014, in the KIPO (Korean Intellectual Property Office). Further, this application is the National Phase Application of International Application No. PCT/KR2015/006971, filed on Jul. 6, 2015, which designates the United States and was published in Korean. Both of the priority documents are hereby incorporated by reference in their entireties.

TECHNICAL FIELD

The present disclosure relates to a wearable device and a method of controlling the wearable device, and more particularly, to a wearable device worn on a user's head to apply an electrical stimulation to a brain or measure brain waves from the brain and a method of controlling the wearable device.

BACKGROUND ART

Brain electrical stimulation technologies using transcranial Direct Current Stimulation (tDCS) have been known to be effective on improvement of cognitive ability and mental illness treatments such as depression and Attention Deficit Hyperactivity Disorder (ADHD).

Furthermore, according to electroencephalogram (EEG) technology, brain activities may be expected by measuring a change in the electric potential of scalp according to brain activities.

Thus, if the brain electrical stimulation technology can be used in everyday life, brain function may be improved and continuous mental disorders may be treated by activating or inhibiting neuronal connections. Furthermore, if the EEG technology can be used in everyday life, functional abnormalities of the brain, occurrence of seizures, infection, or metabolic diseases may be identified.

DISCLOSURE

Technical Problem

However, a conventional electrical stimulation apparatus is mainly configured to directly attach a patch to a flexible strap or head cap and then manually adjust the stimulation intensity of the electrical stimulation apparatus. Also, an electroencephalogram (EEG) device is configured to measure brain waves by attaching the patch directly to a flexible strap or head cap. Therefore, the conventional electrical stimulation device and the EEG device are only used intermittently by experts, and ordinary persons who do not have expert knowledge on the configuration and position of the brain and an allowable amount of current could not use the electrical stimulation device and the EEG device in everyday life due to the risk of a safety accident caused by misoperation.

It is an object of the present disclosure to provide a wearable device which may be safely used in everyday life by ordinary users having no expert knowledge, and to a method of controlling the wearable device.

It is another object of the present disclosure to provide a wearable device which may recognize and identify users so that management of data by users is possible, and to a method of controlling the wearable device.

It is another object of the present disclosure to provide a wearable device which may start an electrical stimulation or measurement of brain waves using the wearable device after correct wear of the wearable device is checked so that user's safety accidents may be prevented, and to a method of controlling the wearable device.

The technical problems of the present disclosure are not limited to the above-mentioned technical objects, and other technical objects which are not mentioned can be clearly understood by those skilled in the art from the following description.

Technical Solution

In accordance with one aspect of the present disclosure, a wearable device, which is worn on a head of a user and applies an electrical stimulation to a brain of the user or measures brain waves from the brain of the user, includes a wearing identification unit checking a worn state of the wearable device by using a first sensor module for sensing the worn state of the wearable device by the user, an electrode unit applying an electrical stimulation to the brain of the user or measuring brain waves from the brain of the user, and a control unit controlling the electrode unit to start the electrical stimulation or the brain wave measurement based on a result of the checking by the wearing identification unit.

In accordance with another aspect of the present disclosure, a method of controlling a wearable device, in which the wearable device is worn on a head of a user and an electrical stimulation is applied to brain or brain waves from the brain are measured, includes checking a worn state of the wearable device by using a first sensor module for sensing a worn state of the wearable device by a user, and controlling the wearable device to start applying an electrical stimulation to the brain or measuring brain waves from the brain, based on a result of the checking operation.

Advantageous Effects

According to the present disclosure, since the electrical stimulation or brain wave measurement is started after checking the wearing state of a user, ordinary users without expert knowledge can safely use a wearable device in daily life.

According to the present disclosure, since users are identified and stored as information on the identified users, personal information verification can be possible even if several users use a single wearable device.

Further, according to the present disclosure, since it is possible to inform a user whether or not the user wears a wearable device correctly, a safety accident due to erroneous wearing can be prevented in advance.

BEST MODE

Figure 1:
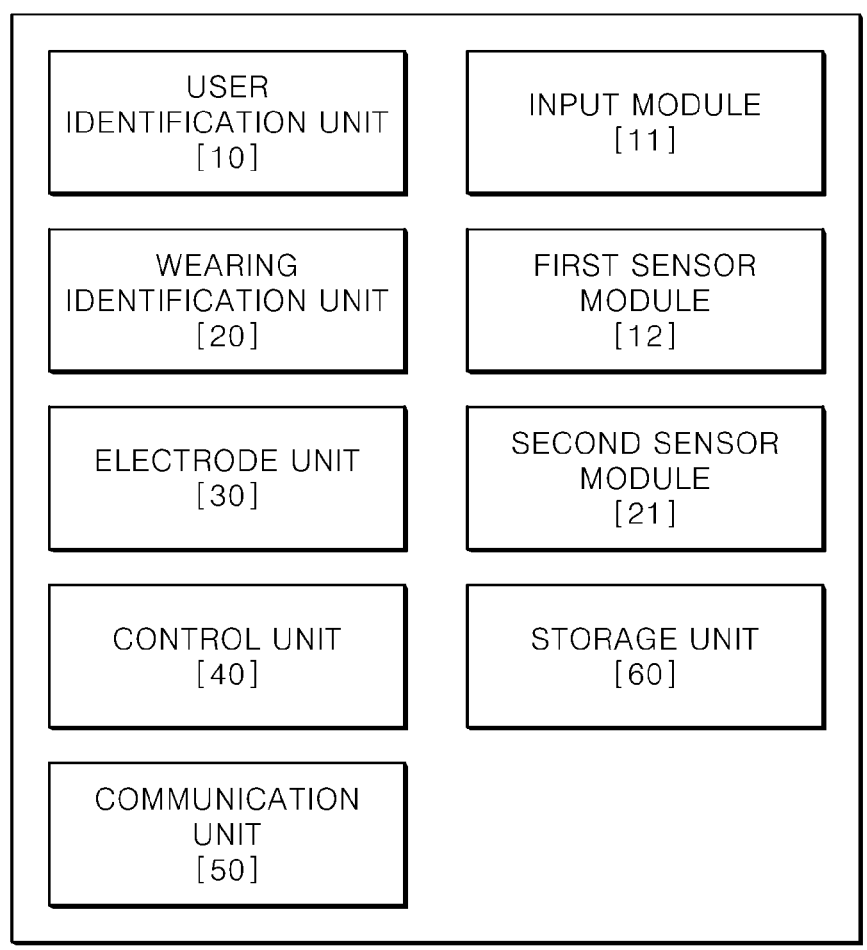
FIG. 1 is a schematic block diagram of a structure of a wearable device according to an embodiment of the present disclosure.

The above objects, features and advantages will become apparent from the detailed description with reference to the accompanying drawings. Embodiments are described in sufficient detail to enable those skilled in the art to easily practice the technical idea of the present disclosure. Detailed descriptions of well-known functions or configurations may be omitted in order not to unnecessarily obscure the gist of the present disclosure. Hereinafter, embodiments of the present disclosure will be described in detail with reference to the accompanying drawings. Throughout the drawings, like reference numerals refer to like elements.

Unless defined otherwise, all terms used herein (including technical or scientific terms) have the same meanings as those generally understood by those of ordinary skill in the art to which the present inventive concept may pertain. The terms as those defined in generally used dictionaries are construed to have meanings matching that in the context of related technology and, unless clearly defined otherwise, are not construed to be ideally or excessively formal.

Terms used in the present specification are used for explaining a specific embodiment, not for limiting the present inventive concept. Thus, an expression used in a singular form in the present specification also includes the expression in its plural form unless clearly specified otherwise in context. It will be further understood that the terms "comprises" and/or "comprising" used herein specify the presence of stated features or components, but do not preclude the presence or addition of one or more other features or components.

Terms such as "portion" or "module" stated in the specification may signify a unit having a hardware configuration, but a part of the unit may be a function portion embodied by software.

Furthermore, the term "wear" state in the specification may be understood as one including a meaning of "attach" or "mount" extending from the original meaning thereof.

Hereinafter, a wearable device according to embodiments of the present disclosure is described with reference to the accompanying drawings.

Figure 2:
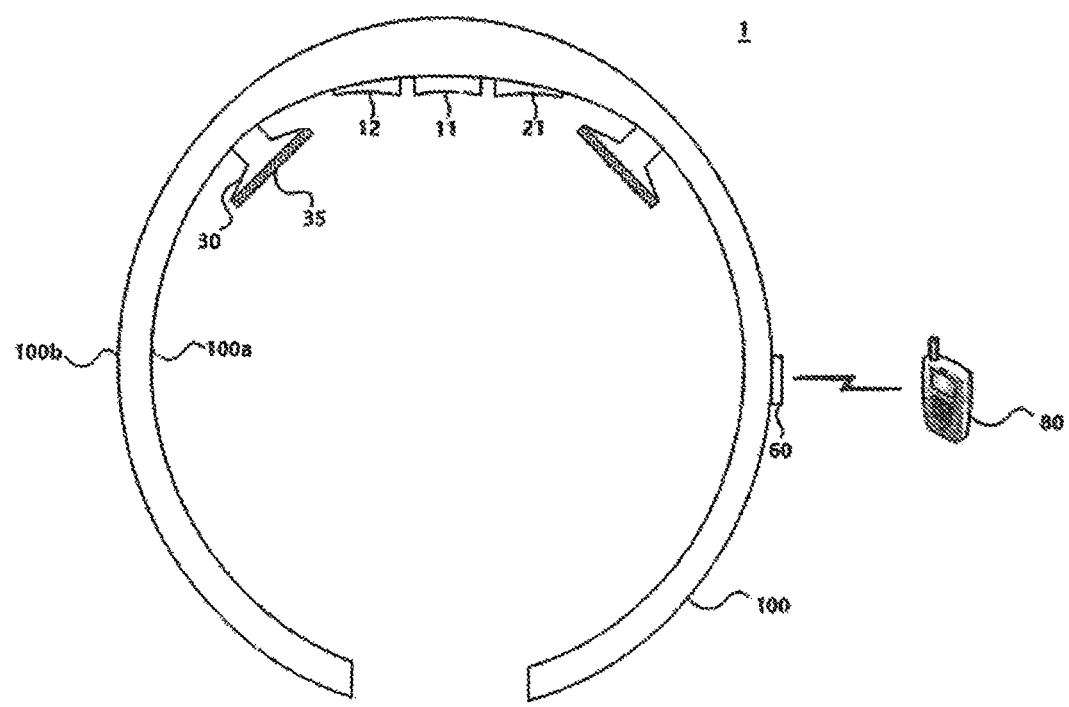
FIG. 2 is a plan view of the wearable device of FIG. 1.
Figure 3:
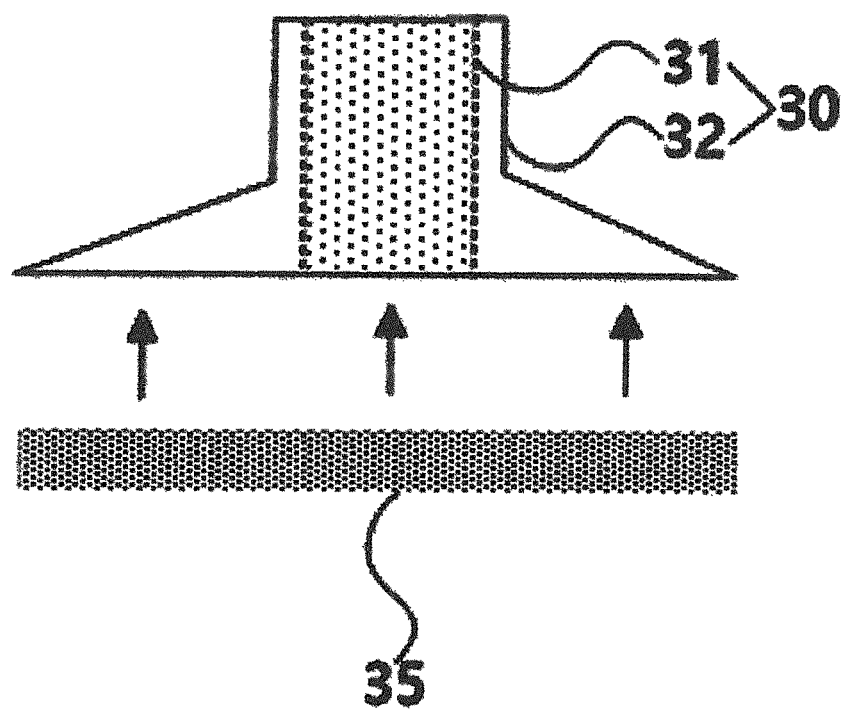
FIG. 3 schematically illustrates a structure of an electrode unit included in the wearable device of FIG. 2.
Figure 4:
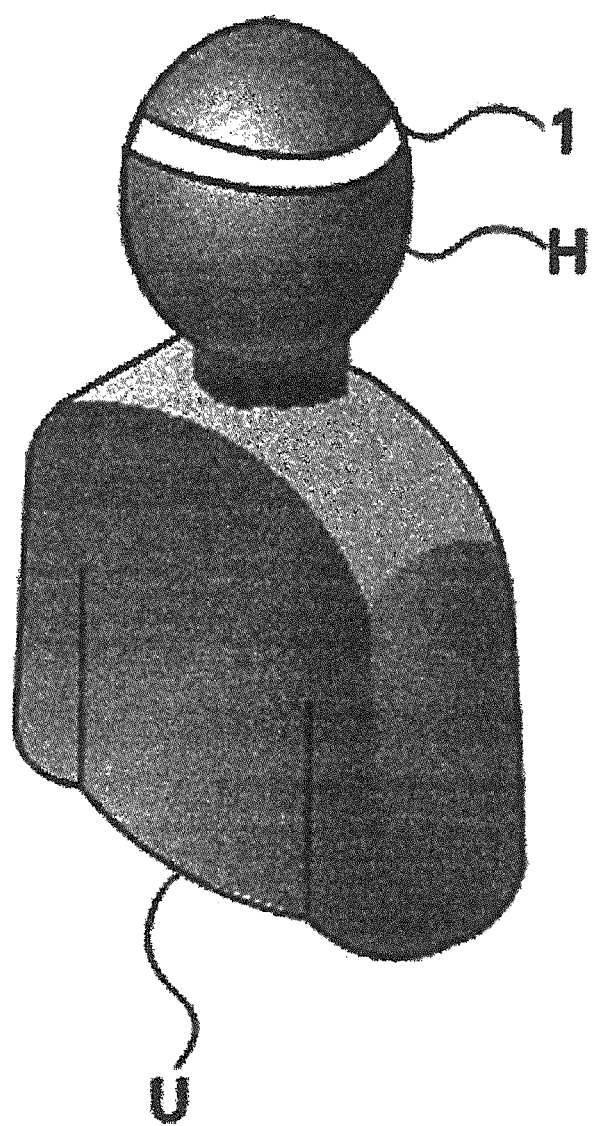
FIG. 4 is a perspective view showing that the wearable device of FIG. 2 is worn on a head.
Figure 5:
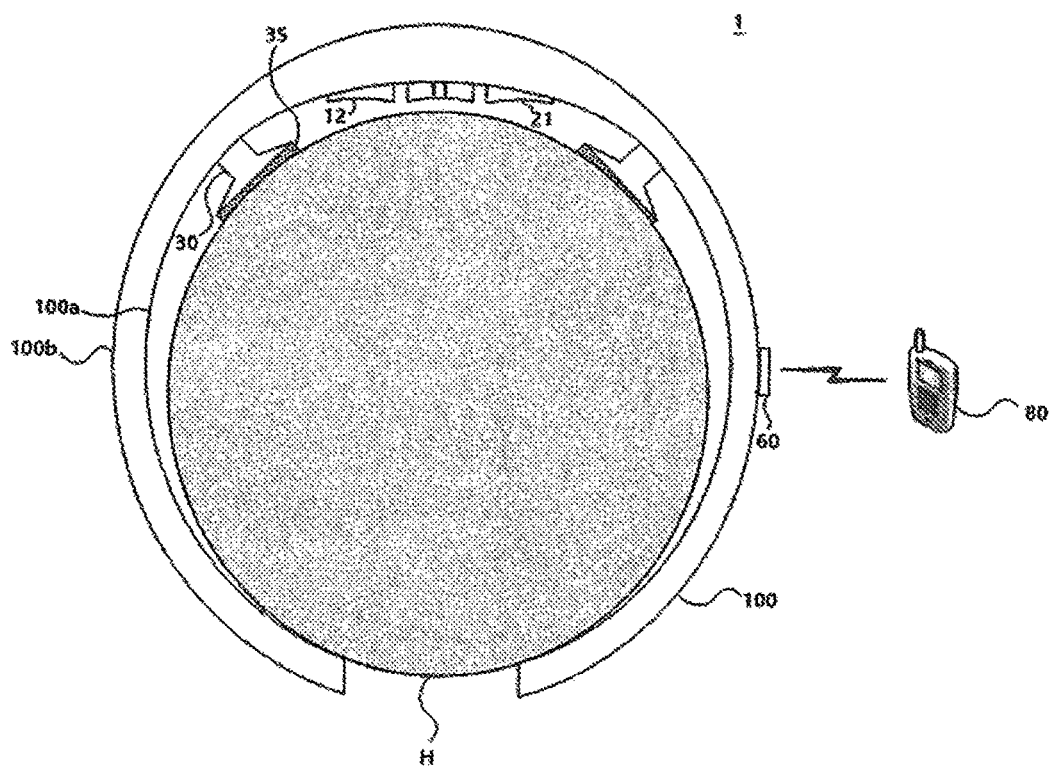
FIG. 5 is a plan view showing that the wearable device of FIG. 2 is worn on a head.
Figure 6:
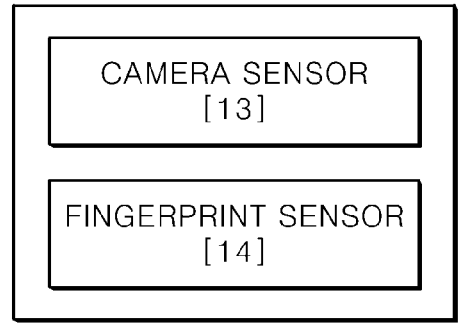
FIG. 6 is a schematic block diagram of a structure of a first sensor module of FIG. 1.
Figure 7:
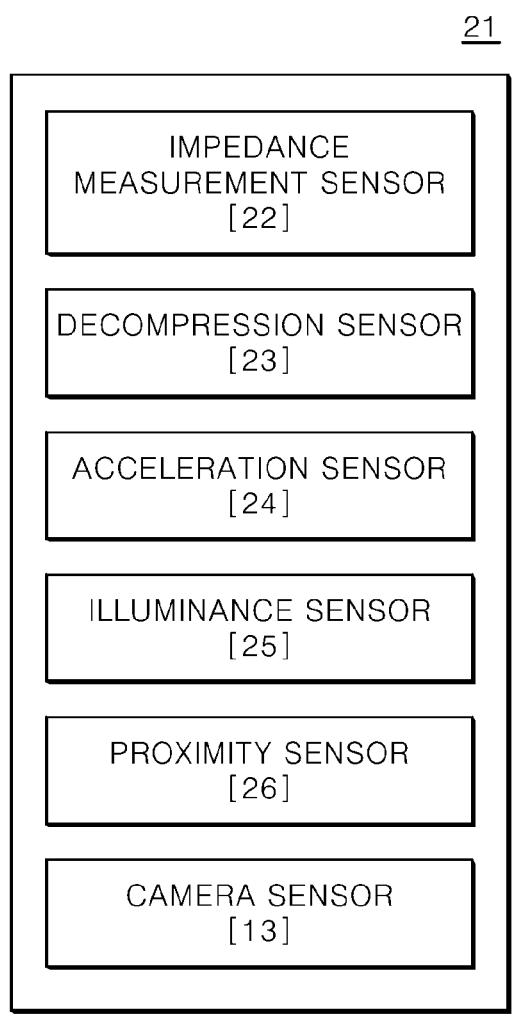
FIG. 7 is a schematic block diagram of a structure of a second sensor module of FIG. 1.
Figure 8:
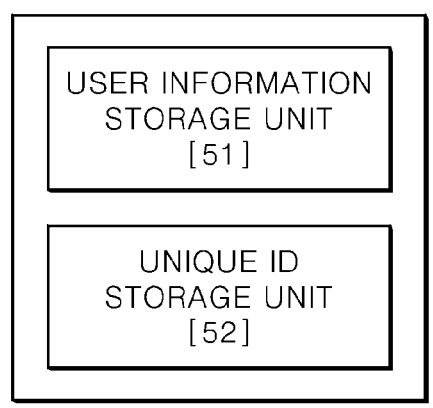
FIG. 8 is a schematic block diagram of a structure of a storage unit of FIG. 1.

First, referring to FIGS. 1 to 8, a wearable device 1 according to an embodiment of the present disclosure is described. FIG. 1 is a schematic block diagram of a structure of the wearable device 1 according to an embodiment of the present disclosure. FIG. 2 is a plan view of the wearable device 1 of FIG. 1. FIG. 3 schematically illustrates a structure of an electrode unit 30 included in the wearable device 1 of FIG. 2. FIG. 4 is a perspective view showing that the wearable device 1 of FIG. 2 is worn on a head H. FIG. 5 is a plan view showing that the wearable device 1 of FIG. 2 is worn on the head H. FIG. 6 is a schematic block diagram of a structure of a first sensor module 12 of FIG. 1. FIG. 7 is a schematic block diagram of a structure of a second sensor module 21 of FIG. 1. FIG. 8 is a schematic block diagram of a structure of a storage unit 50 of FIG. 1.

Referring to FIGS. 1 to 5, the wearable device 1 according to the present embodiment, which is worn on the head H of a user U, may apply an electrical stimulation to the brain of the user U or measure brain waves of the user U from the brain. In other words, the wearable device 1 may be operated as an electrical stimulation apparatus or an electroencephalogram (EEG) device, as necessary. In detail, when the user U wears the wearable device 1 on the head H, a patch 35 attached to the electrode unit 30 may contact a particular position of the head H that is a target. Then, a current flows at the particular position of the head H of the user U via the patch 35 so that an electrical stimulation may be applied to a brain area to be a target or brain waves from the particular position of the head H of the user U may be measured via the patch 35.

However, the wearable device 1 according to the present embodiment may include a user identification unit 10 for identifying the user U and a wearing identification unit 20 for identifying a worn state of the wearable device 1. Accordingly, after the user identification unit 10 identifies the user U and the wearing identification unit 20 checks that the wearable device 1 is normally worn, the wearable device 1 may start applying an electrical stimulation to the brain of the user U or measuring the brain waves of the user U. However, when the wearable device 1 includes only one of the user identification unit 10 and the wearing identification unit 20, either after the user identification unit 10 identifies the user U or after the wearing identification unit 20 checks that the wearable device 1 is normally worn, the wearable device 1 may start applying an electrical stimulation to the brain of the user U or measuring the brain waves of the user U.

Accordingly, according to the wearable device 1 according to the present embodiment, a result of use of the wearable device 1 with respect to the identified user U may be stored and managed and a safety accident due to erroneous wear may be prevented in advance.

In detail, referring to FIGS. 1 and 2, the wearable device 1 may include the user identification unit 10, the wearing identification unit 20, the electrode unit 30, and a control unit 40, and in some embodiments, may further include a storage unit 50, a communication unit 60, an input module 11, a first sensor module 12, and a second sensor module 21. However, since the elements illustrated in FIGS. 1 and 2 are not essential elements, the wearable device 1 having elements more or less than those illustrated in FIGS. 1 and 2 may be implemented. Although FIG. 2 illustrates the wearable device 1 of FIG. 1 for convenience of explanation, the shape of the wearable device 1 according to the present embodiment is not limited to the shape illustrated in FIG. 2.

For reference, referring to FIG. 2, the wearable device 1 may include a frame 100 that is wearable on the head H. The frame 100 is a frame of the wearable device 1, and various elements forming the wearable device 1 may be coupled to the frame 100 or included in the frame 100. The frame 100 may include a first surface 100a facing the head H and a second surface 100b located at the opposite side to the first surface 100a. Furthermore, since the frame 100 may be worn on the head H of the user U, the user U may use the wearable device 1 by wearing the wearable device 1 on the head H. Accordingly, if the frame 100 has a shape to be worn on the head H of the user U, the shape of the frame 100 is not limited thereto.

For example, referring to FIG. 2, although the frame 100 may have a ring structure with one side open, but the present disclosure is not limited thereto. Since one side of the frame 100 is open, the frame 100 may spread outwardly according to the size of the head H of the user U so as to be worn on the head H of the user U. Furthermore, when the frame 100 is worn on the head H of the user U, the frame 100 may press the head H so that the frame 100 may not fall down and be stably fixed to the head H. In some cases, as a partial area of the frame 100 is supported by an auricle of the user U, the frame 100 may be stably worn on the head H, but the present disclosure is not limited thereto.

The respective elements are described below in detail.

First, the user identification unit 10 may identify the user U by using the input module 11 for receiving an input of information about the user U from the user U or the first sensor module 12 for sensing the user U. For the identification of a user, the storage unit 50 may previously store information about the user U. For example, information about a user account or information about the physical properties of the user U including a face shape or a fingerprint may be previously stored, but the present disclosure is not limited thereto.

In other words, the user identification unit 10 may recognize and identify the user U by comparing the information about the use U input from the input module 11 or the information about the physical properties of the user U sensed through the first sensor module 12 with the information about the user U stored in the storage unit 50. The function of the user identification unit 10 may be understood as a login process of the wearable device 1. Accordingly, according to the wearable device 1 according to the present embodiment, the use of the wearable device 1 by the user U who is not previously registered may be restricted, and a plurality of the users U using the same wearable device 1 may be distinguished through the user identification.

The input module 11 may receive an input of information about the user U from the user U. For example, the user U may input a user account through the input module 11. Since information about previously registered user accounts may be previously stored in the storage unit 50, the user identification unit 10 may identify the user U by searching the storage unit 50 for a user account corresponding to the user account input through the input module 11. In other words, when the corresponding user account is found from the storage unit 50, the user identification may be completed. When the corresponding user account is not found from the storage unit 50, the user identification may fail. However, the information input to the input module 11 is not limited to the user account, and any information used to identify the user U may be input through the input module 11.

Furthermore, the input module 11 may have a hardware structure such as a touch screen or an input button to directly receive an input from the user U, but the present disclosure is not limited thereto.

In some embodiments, the input module 11 may function as a manipulation module for controlling the operation of the wearable device 1. To this end, the input module 11 may receive an input of manipulation information in addition to the information about the user U from the user U. For example, the input module 11 may receive inputs of manipulation information about whether power is applied and manipulation information about the strength of current flowing in the electrode unit 30 during an electrical stimulation.

Accordingly, the user U may control the wearable device 1 through the input module 11 as necessary.

However, the frame 100 may include the first surface 100a facing the head H and the second surface 100b located at the opposite side to the first surface 100a. The input module 11 may be formed on the first surface 100a of the frame 100. In other words, since the input module 11 is located on the first surface 100a that is a wear side of the frame 100, when the user U wears the wearable device 1, manipulation of the wearable device 1 may be prevented during the progress of an electrical stimulation or a brain wave measurement so that the manipulation of the wearable device 1 may be possible only when the wearable device 1 is not worn on the head H. Accordingly, according to the wearable device 1 according to some embodiments, side effects and safety accidents due to malfunction of the wearable device 1 may be reduced.

The first sensor module 12, referring to FIG. 6, may include at least one of a camera sensor 13 and a fingerprint sensor 14. The camera sensor 13 may sense the face of the user U or a relatively location of the wearable device 1 worn on the head H of the user U. In detail, the camera sensor 13 may recognize the face of the user U through image processing, and sense a position of the wearable device 1 in the head H of the user U through the head H or face of the user U recognized when the wearable device 1 is worn. Furthermore, the fingerprint sensor 14 may sense a fingerprint of the user U.

However, referring to FIG. 5, in some embodiments, the camera sensor 13 that senses the face of the user U may not be included in the wearable device 1, but may be included in an external device such as a communication terminal 80. In other words, the user identification unit 10 may receive from the external device information sensed by the camera sensor of the external device through the communication unit 60, and use the received information. For example, an image of the user U captured by the camera sensor of the communication terminal 80 may be transmitted to the wearable device 1 and used by the user identification unit 10, but the present disclosure is not limited thereto.

Accordingly, the user identification unit 10 may identify the user U through at least one of the sensed face and fingerprint of the user U. In detail, the storage unit 50 may previously store information about the user U such as the information about user accounts or the information about the physical properties of the user U including a face shape or a fingerprint. Accordingly, the user identification unit 10 may identify the user U by searching the storage unit 50 for information corresponding to the face or fingerprint of the user U sensed by the first sensor module 12.

When the corresponding information about the user U is found from the storage unit 50, the user identification may be completed. Accordingly, it may be identified that the wearable device 1 is used by the user U of a user account having the found user information.

The wearing identification unit 20 may check a worn state of the wearable device 1 by using the second sensor module 21 for sensing the worn state of the wearable device 1 by the user U. In detail, wearing identification unit 20 may check whether the wearable device 1 is worn in a correct direction based on the information sensed by the second sensor module 21. In other words, the wearing identification unit 20 may check whether the user U wears the wearable device 1 with the frame 100 turned sideways or flipped vertically, and whether the wearable device 1 is worn such that the electrode unit 30 contacts a target position.

The second sensor module 21, referring to FIG. 7, may include at least one of an impedance measurement sensor 22, a decompression sensor 23, an acceleration sensor 24, an illuminance sensor 25, a proximity sensor 26, and the camera sensor 13. The camera sensor 13 may be used by the first sensor module 12 and the second sensor module 21, as necessary.

The impedance measurement sensor 22 may measure impedance through the electrode unit 30. In detail, when the user U wears the wearable device 1, the patch 35 attached to the electrode unit 30 contacts the head H so that the impedance measurement sensor 22 may measure bioimpedance or electrode impedance through the electrode unit 30. Since there is an impedance value expected when the user U correctly wears the wearable device 1, when a measurement result of the impedance measurement sensor 22 is within a preset value range, whether the user U correctly wears the wearable device 1 so that the patch 35 closely contacts the target position may be determined.

The decompression sensor 23 may measure pressure applied to the wearable device 1. For example, when the user U wears the wearable device 1, since the frame 100 may be fixed to the head H by pressing the head H, pressure may be applied from the head H of the user U to the wearable device 1. Accordingly, as a degree of the pressure applied to the wearable device 1 is measured by using the decompression sensor 23, when a measured pressure is over a preset pressure, it may be determined that the user U correctly wears the wearable device 1.

The acceleration sensor 24 may measure acceleration of the wearable device 1. A direction in which the wearable device 1 faces may be identified through the acceleration measured through the acceleration sensor 24. Accordingly, it may be sensed based on the measured acceleration whether the wearable device 1 is worn upside down.

The illuminance sensor 25 is located on a particular surface of the wearable device 1 and measures external illuminance so as to sense whether the surface closely contacts skin. In other words, according to the illuminance sensor 25, a degree of the wearable device 1 contacting the skin may be measured. Accordingly, since whether the wearable device 1 closely contact the skin may be determined by using the illuminance measured by the illuminance sensor 25, it may be sensed whether the wearable device 1 is normally worn.

The proximity sensor 26 may be located on a particular surface of the wearable device 1 and sense whether the wearable device 1 is normally worn by measuring a degree of proximity of the skin to the particular skin. In other words, a skin distance of the wearable device 1 (a distance between the wearable device 1 and the skin) may be measured by the proximity sensor 26. Accordingly, it may be determined based on the degree of proximity (proximity distance) measured by the proximity sensor 26 whether the wearable device 1 is normally worn.

The camera sensor 13 may capture an image of the user U wearing the wearable device 1. Accordingly, it may be determined by analyzing a captured image whether the wearable device 1 is worn at an intended normal position.

Accordingly, the wearing identification unit 20 may identify the worn state of the wearable device 1 by checking a wearing position and a wearing direction of the wearable device 1 based on at least one of the measured impedance, the measured pressure, the measured acceleration, the measured illuminance, the measured distance, and the captured image.

However, referring to FIG. 5, in some embodiments, the camera sensor capturing an image of the user U wearing the wearable device 1 may not be included in the wearable device 1, but may be included in an external device such as the communication terminal 80. In other words, the user identification unit 10 may receive from the external device information sensed by the camera sensor of the external device through the communication unit 60, and use the received information. For example, the image of the user U captured by the camera sensor of the communication terminal 80 is transmitted to the wearable device 1 to be used by the wearing identification unit 20, but the present disclosure is not limited thereto.

The electrode unit 30 may apply an electrical stimulation to the brain of the user U or measure brain waves from the brain of the user U. Referring to FIGS. 2 and 3, the electrode unit 30 may include an inner electrode 31 formed of a conductive member and an outer electrode 32 surrounding at least a part of the inner electrode 31 and formed of an insulating member. One end of the electrode unit 30 may be connected and fixed to the frame 100. In detail, one end of the electrode unit 30 may be connected and fixed to the first surface 100$a$ of the frame 100.

The inner electrode 31 is an internal area of the electrode unit 30 and may be formed of a conductive member. Although the conductive member is a metal member, the present disclosure is not limited thereto. In detail, current may be applied to the inner electrode 31 from a power unit (not shown) of the frame 100. The received current may be transmitted to the patch 35. Furthermore, the inner electrode 31 may receive the brain waves from the patch 35.

The outer electrode 32 is an external area of the electrode unit 30 and may be formed of an insulating member. The insulating member may include plastic, but the present disclosure is not limited thereto. In detail, since the outer electrode 32 may surround at least a part of the inner electrode 31 and the outer electrode 32 surrounds the inner electrode 31, even when current flows in the inner electrode 31, the wearable device 1 may be safely used.

The patch 35, referring to FIGS. 2 and 3, is detachable to the electrode unit 30, and when the patch 35 is attached to the electrode unit 30, the patch 35 contacts the head H and may transmit brain waves or current. The patch 35 may be attached to the electrode unit 30 by using an adhesive and may be removed after use.

The patch 35 may include chlorine ions. Accordingly, when the patch 35 contacts the head H, impedance of a skin interface is lowered so that the occurrence of pain during an electrical stimulation may be prevented. Since the patch 35 may be in a solid state or a gel state, no electrolyte needs to be separately coated on the scalp during the electrical stimulation, and referring to FIG. 5, the patch 35 may be bent corresponding to the shape of the head H.

The control unit 40 may control an overall operation of the wearable device 1. For example, the control unit 40 may control the electrode unit 30 to start an electrical stimulation or a brain wave measurement based on the result of identification by the user identification unit 10 and the result of checking by the wearing identification unit 20. In detail, when the user U is identified according to the result of identification by the user identification unit 10 and the worn state of the wearable device 1 is checked to be a normal worn state according to the result of checking by the wearing identification unit 20, the control unit 40 may control the electrode unit 30 to start an electrical stimulation or a brain wave measurement.

According to the wearable device 1 of the present embodiment, since the wearable device 1 operates after the user identification is made, a result of use of the wearable device 1 may be stored and managed with respect to the identified user U. Even when a plurality of users U use the single wearable device 1, management of personal information may be possible. Furthermore, since the user U who is not identified may be restricted to use the wearable device 1, a safety accident due to a misuse of the wearable device 1 may be prevented.

Furthermore, according to the wearable device 1 of the present embodiment, the checking of the user identification and the worn state of the wearable device 1 may be used as a trigger of an electrical stimulation or a brain wave measurement. Accordingly, a safety accident of the user U due to the use of the wearable device 1 may be prevented.

The storage unit 50 may store information needed for using the wearable device 1. Referring to FIG. 8, the storage unit 50 may include a user information storage unit 51 and a unique identification (ID) storage unit 52. The user information storage unit 51 may store information about the user U, for example, information about user accounts or information about the physical properties of the user U including a face shape or a fingerprint.

In addition, the user information storage unit 51 may store a result of the electrical stimulation or the brain wave measurement performed by the electrode unit 30, and a result of the sensing performing by the first and second sensor modules 12 and 21, as the information about the identified user U, but the present disclosure is not limited thereto and time, noise, illuminance, temperature, location, information about the analysis of surroundings through a rear camera, and information about whether peripheral appliances are operating or not may be automatically collected during the operation of the wearable device 1 and stored in the user information storage unit 51 with the operation information of the wearable device 1.

In other words, since the information about the physical properties and the information about the use of the wearable device 1 may be integrally managed in the user information storage unit 51 with respect to a user account, even when the wearable device 1 is used by a plurality of users U, personal information management may be possible. Furthermore, since the result of an electrical stimulation or brain wave measurement is stored with the result of the sensing performed by the first and second sensor modules 12 and 21 and time, noise, illuminance, temperature, location, information about the analysis of surroundings through a rear camera, and information about whether peripheral appliances are operating or not, when an excessive movement of the user U is sensed during an electrical stimulation or a brain wave measurement, the movement may be determined to be noise information and thus abundant pieces of information may be used for a medical use.

The unique ID storage unit 52 may store a unique ID of the wearable device 1. The unique ID of the wearable device 1 may be transmitted to the external device together when the information about the identified user U stored in the user information storage unit 51 is transmitted to the external device. Accordingly, when the external device receives information, it may be checked from which wearable device the information is transmitted.

The communication unit 60 may communicate with the external device including the communication terminal 80, and there is no limit in a communication method used by the communication unit 60.

As described above, according to the wearable device 1 according to the present disclosure, since an electrical stimulation or a brain wave measurement is started after the worn state of the user U is checked, the user U who is an ordinary person having no expert knowledge may safely use the wearable device 1 in everyday life.

Figure 9:
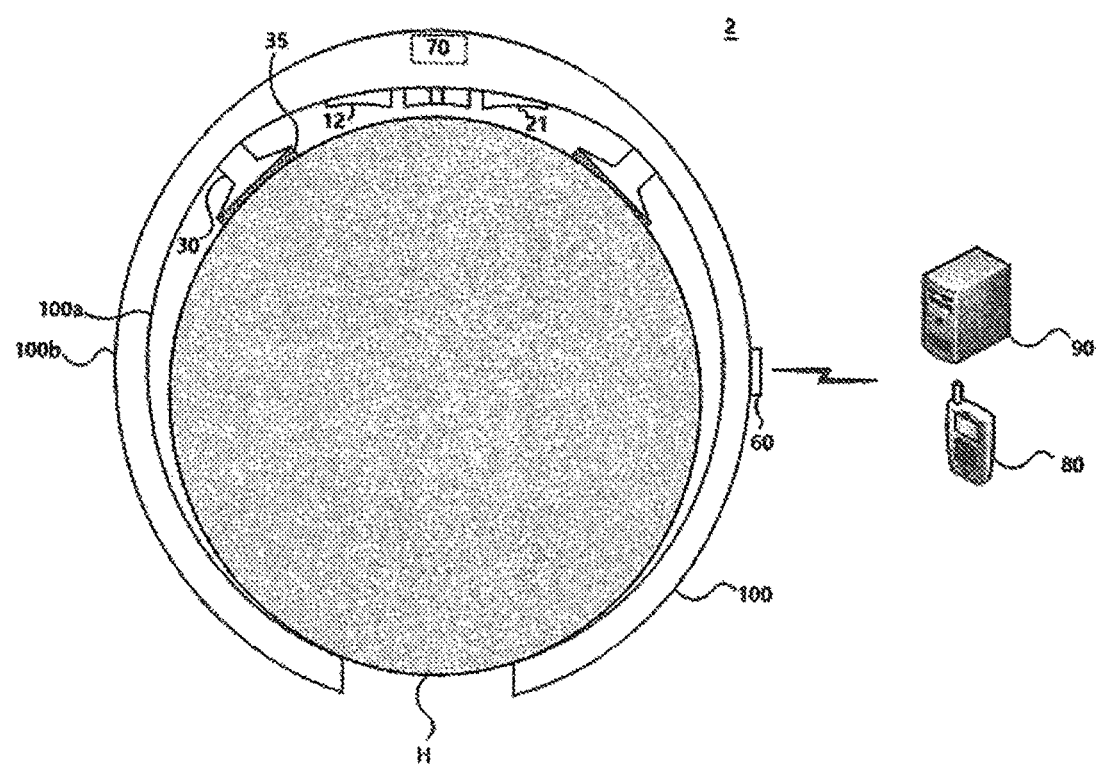
FIG. 9 is a schematic plan view of a structure of a wearable device according to another embodiment of the present disclosure.

A wearable device 2 according to another embodiment of the present disclosure is described with reference to FIG. 9. Referring to FIG. 9, a structure of the wearable device 2 according to the present embodiment is schematically illustrated. However, differences from the wearable device 1 according to the above-described embodiment are mainly discussed below.

Referring to FIG. 9, the wearable device 2 may include the communication unit 60 and a warning module 70. The communication unit 60 may communicate with an external device such as the communication terminal 80 or a management server 90. For example, the communication unit 60 may transmit to the external device the information about the identified user U stored in the storage unit 50 with the unique ID of the wearable device 2.

When the worn state of the user U is determined to be incorrect based on a result of checking by the wearing identification unit 20, the warning module 70 may notify the user U of such a fact. For example, the warning module 70 may include a speaker, a vibrator, and a light-emitting element. The control unit 40 may control the warning module 70 such as the speaker, the vibrator, and the light-emitting element and may give a feedback to the user U.

For example, the control unit 40 may generate a warning sound by controlling the speaker, or guide the user U to correctly wear the wearable device 2. Furthermore, the control unit 40 may generate vibrations by controlling the vibrator to notify the user U of an incorrect worn state. A vibration type according to the incorrect wear notification may be preset. The control unit 40 may notify the user U of an incorrect worn state by controlling the light-emitting element to generate light. A light emission type according to the incorrect wear notification may be preset.

However, the present disclosure is not limited thereto and the control unit 40 may notify an incorrect worn state to the external communication terminal 80 by controlling the communication unit 60. The user U may check the worn state of the wearable device 2 by checking the external communication terminal 80.

Accordingly, according to the wearable device 2 of the present embodiment, since the user U may directly check whether the worn state of the wearable device 2 is incorrect, danger of a safety accident due to an incorrect wear of the wearable device 2 may be reduced.

When the wearable device 2 continues to be incorrectly worn even after a preset time passes after the incorrect wear of the wearable device 2 is checked, the control unit 40 may stop the electrical stimulation or brain wave measurement to prevent a safety accident in advance.

Figure 10:
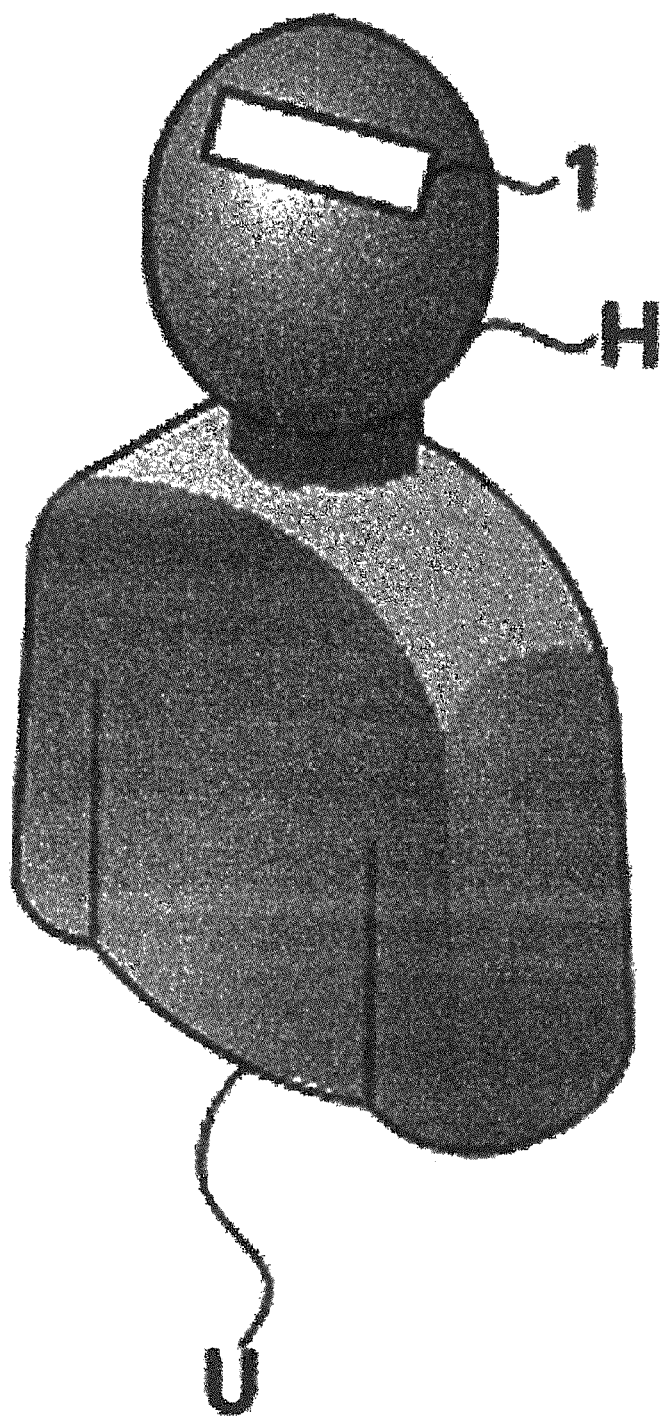
FIG. 10 is a schematic perspective view of a structure of a wearable device according to another embodiment of the present disclosure.

A wearable device 3 according to another embodiment of the present disclosure is described with reference to FIG. 10. Referring to FIG. 10, a structure of the wearable device 3 according to the present embodiment is schematically illustrated. However, differences from the wearable device 1 according to the above-described embodiment are mainly discussed below.

The wearable device 3 illustrated in FIG. 10 is different in the shape from the wearable device 1 of FIG. 2 having a frame shape. In other words, referring to FIG. 10, the wearable device 3 may have a patch shape and may be worn on (attached to) the head H of the user U. However, since the wearable device 3 may include at least a part of the elements illustrated in FIG. 1, the wearable device 3 has no substantial difference from the wearable device 1 in terms of structure, except for the shape.

Figure 11:
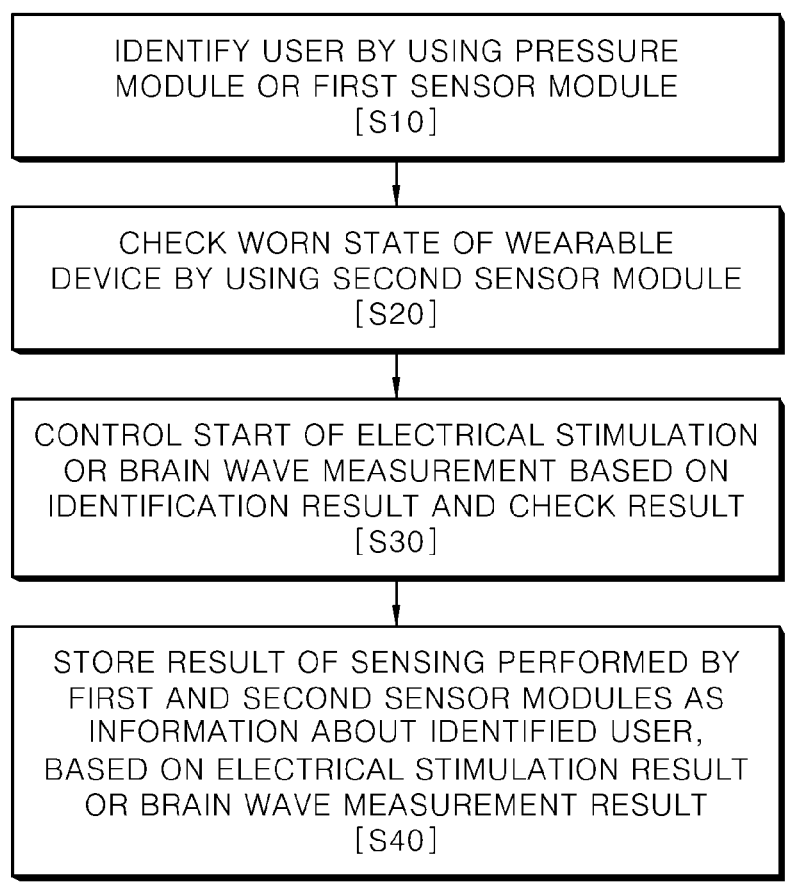
FIG. 11 is a flowchart of a method of controlling a wearable device according to an embodiment of the present disclosure.

A method of controlling the wearable device 1 according to the present embodiment is presented below. FIG. 11 illustrates a flowchart of a method of controlling the wearable device 1 according to the present embodiment. However, descriptions about portions redundant with those of the wearable device 1 are omitted.

In the method of controlling the wearable device 1 according to the present embodiment, in which the wearable device 1 is worn on the head H of the user U and an electrical stimulation is applied to the brain of the user U or brain waves from the brain are measured, the user U may be identified by using the input module 11 for receiving an input of information about the user U from the user U or the first sensor module 12 for sensing the user U (S10).

The identification of the user U may be understood as a login process to the wearable device 1. A plurality of users U using the same wearable device 1 may be distinguished through the user identification operation.

The identification of the user U by using the input module 11 or the first sensor module 12 may include searching of whether information about the user U input by the user U through the input module 11 or information corresponding to the information about the user U sensed through the first sensor module 12 is present in the storage unit 50. If appropriate information is found as a result of the search, it may be said that the user U is identified.

Since the first sensor module 12 may include at least one of the camera sensor 13 and the fingerprint sensor 14, the sensing of the user U through the first sensor module 12 may include sensing of the face or fingerprint of the user U through the first sensor module 12.

Next, the worn state of the wearable device 1 may be checked by using the second sensor module 21 for sensing the worn state of the wearable device 1 by the user U (S20).

The checking of the worn state of the wearable device 1 by using the second sensor module 21 may signify checking whether the wearable device 1 is worn in a correct direction, based on the information sensed through the second sensor module 21. In the above operation, it may be checked whether the user U wears the wearable device 1 with the frame 100 turned sideways or flipped vertically, and whether the wearable device 1 is worn such that the electrode unit 30 contacts a target position.

Since the second sensor module 21 may include at least one of the impedance measurement sensor 22, the decompression sensor 23, and the acceleration sensor 24, the worn state of the wearable device 1 may be identified by checking the wearing position or direction of the wearable device 1 based on at least one of the measured impedance, the measured pressure, and the measured acceleration.

Next, the wearable device 1 may be controlled to start applying an electrical stimulation to the brain of the user U or measuring brain waves from the brain, based on the results of the identification operation and the checking operation (S30).

In other words, when the user U is identified and it is checked that the identified user U correctly wears the wearable device 1, the wearable device 1 may be controlled to start an electrical stimulation or a brain wave measurement. Accordingly, a safety accident due to incorrect wearing of the wearable device 1 may be prevented.

Next, a result of the electrical stimulation, a result of the brain wave measurement, and a result of the sensing performed by the first and second sensor modules 12 and 21 may be stored as the information about the identified user U (S40).

However, the information to be stored is not limited thereto and time, noise, illuminance, temperature, location, information about the analysis of surroundings through a rear camera, and information about whether peripheral appliances are operating or not may be automatically collected during the operation of the wearable device 1 and stored with the operation information of the wearable device 1. Accordingly, when an excessive movement of the user U is sensed during the electrical stimulation or brain wave measurement, the movement may be determined to be noise information and thus abundant pieces of information may be used for a medical use.

Furthermore, the method may be performed by omitting any one of the identification of the user U(S10) and the checking of the worn state of the wearable device 1 (S20), as necessary. In this case, the wearable device 1 may be controlled to start applying an electrical stimulation to the brain of the user U or measuring brain waves from the brain, based on the result of the identification operation (S10) or the result of the checking operation (S20).

The present disclosure described above may be variously substituted, altered, and modified by those skilled in the art to which the present invention pertains without departing from the scope and sprit of the present disclosure. Therefore, the present disclosure is not limited to the above-mentioned exemplary embodiments and the accompanying drawings.

The invention claimed is:

1. A wearable device, which is worn on a head of a user and applies an electrical stimulation to a brain of the user or measures brain waves from the brain of the user, the wearable device comprising:

a first sensor module configured to sense a wearing state of the wearable device by the user;

a wearing identification unit configured to check the wearing state of the wearable device based on information sensed from the first sensor module;

a second sensor module configured to sense an identification of the user;

a user identification unit having an input module and a storage unit storing information on a user account that is previously registered, and configured to identify the user based on the sensed identification of the user and the stored information on the user account;

an electrode unit configured to apply an electrical stimulation to the brain of the user and measure brain waves from the brain of the user; and a control unit configured to control the electrode unit to start the electrical stimulation or the brain wave measurement, wherein when a corresponding user account stored in the storage unit is identified based on the sensed identification of the user from the second sensor and the wearable device is worn in predetermined correct direction based on the information sensed from the first sensor module, the control unit controls the electrode unit to start the electrical stimulation or the brain wave measurement, and wherein the first sensor module comprises at least one of an impedance measurement sensor for sensing impedance through the electrode unit, a decompression sensor for measuring pressure applied to the wearable device, an acceleration sensor for measuring acceleration of the wearable device, an illuminance sensor for measuring skin contact of the wearable device, a proximity sensor for measuring a skin distance of the wearable device, and a camera sensor for capturing an image of the user wearing the wearable device, and the wearing identification unit checks a wearing position or direction of the wearable device based on at least one of a measured impedance, a measured pressure, a measured acceleration, a measured illuminance, a measured distance, and a captured image.

2. The wearable device of claim 1, wherein the second sensor module comprises at least one of a camera sensor for sensing a face of the user and a fingerprint sensor for sensing a fingerprint of the user, and the user identification unit identifies the user through at least one of the face and fingerprint of the user.

3. The wearable device of claim 1, wherein the input module receives an input of the user account from the user, and the user identification unit identifies the user by searching the storage unit for a user account corresponding to the input user account.

4. The wearable device of claim 1, wherein the storage unit configured to store a result of the electrical stimulation performed by the electrode unit, a result of the brain wave measurement, and a result of the sensing performed by the first sensor module and a second sensor module, as information about an identified user.

5. The wearable device of claim 4, further comprising:
a communication unit configured to communicate with an external device,
wherein
the wearable device has a unique identification,
the communication unit configured to transmit, to an external device, the information about the identified user stored in the storage unit with the unique identification of the wearable device.

6. The wearable device of claim 1, wherein the camera sensor is included in an external device, and the wearing identification unit receives sensing information by the camera sensor from the external device.

7. A method of controlling a wearable device having a first sensor module, a wearing identification unit, a second sensor module, a user identification unit having an input module and a storage unit storing information on a user account that is previously registered, an electrode unit and a control unit, the method comprising:

sensing, by the first module, a wearing state of the wearable device by the user;

checking the wearing state of the wearable device based on information sensed from the first sensor module;

sensing, by the second sensor module, the identification of the user;

identifying the user based on the sensed identification of the user and the stored information on the user account;

when a corresponding user account stored in the storage unit is identified based on the sensed identification of the user from the second sensor and the wearable device is worn in predetermined correct direction based on the information sensed from the first sensor module, controlling, by the control unit, the electrode unit to start applying an electrical stimulation to the brain or measuring brain waves from the brain, wherein the first sensor module comprises at least one of an impedance measurement sensor for sensing impedance through the electrode unit, a decompression sensor for measuring pressure applied to the wearable device, an acceleration sensor for measuring acceleration of the wearable device, an illuminance sensor for measuring skin contact of the wearable device, a proximity sensor for measuring a skin distance of the wearable device, and a camera sensor for capturing an image of the user wearing the wearable device, and the wearing identification unit checks a wearing position or direction of the wearable device based on at least one of a measured impedance, a measured pressure, a measured acceleration, a measured illuminance, a measured distance, and a captured image.

8. The method of claim 7, further comprising:
storing, in the storage unit, a result of the electrical stimulation, a result of the brain wave measurement, and a result of the sensing performed by the first sensor module and a second sensor module, as information about an identified user.

* * * * *